United States Patent [19]
Hsu et al.

[11] Patent Number: 5,192,743
[45] Date of Patent: Mar. 9, 1993

[54] RECONSTITUTABLE LYOPHILIZED PROTEIN FORMULATION

[75] Inventors: Chung C. Hsu, Los Altos Hills; Hoc M. Nguyen, San Francisco; Sylvia S. Wu, San Ramon, all of Calif.

[73] Assignee: Genentech, Inc., South San Francisco, Calif.

[21] Appl. No.: 821,206

[22] Filed: Jan. 16, 1992

[51] Int. Cl.$^5$ .................................... A61K 37/02
[52] U.S. Cl. ............................ 514/8; 514/2; 514/12; 514/21; 514/944; 530/427; 604/416
[58] Field of Search .............. 530/427; 514/970, 969, 514/967, 944, 21, 12, 8, 2; 604/416, 87, 88, 92

[56] References Cited

U.S. PATENT DOCUMENTS

| | | | |
|---|---|---|---|
| 3,859,169 | 1/1975 | O'Driscoll et al. | 435/182 |
| 4,609,640 | 9/1986 | Morishita et al. | 514/12 |
| 4,717,717 | 1/1988 | Finkenaur | 514/21 |
| 4,774,091 | 9/1988 | Yamahira et al. | 424/85.1 |
| 4,883,785 | 11/1989 | Chow et al. | 514/31 |
| 4,961,920 | 10/1990 | Ward | 514/12 |
| 5,037,643 | 8/1991 | Green | 514/2 |
| 5,039,540 | 8/1991 | Ecanow | 514/776 |

FOREIGN PATENT DOCUMENTS

| | | |
|---|---|---|
| 0105014 | 4/1984 | European Pat. Off. |
| 0193372 | 9/1986 | European Pat. Off. |
| 0193917 | 9/1986 | European Pat. Off. |
| 0213776 | 3/1987 | European Pat. Off. |
| 0243179 | 10/1987 | European Pat. Off. |
| 0261599 | 3/1988 | European Pat. Off. |
| 0267015 | 5/1988 | European Pat. Off. |
| 0308238 | 3/1989 | European Pat. Off. |
| 0312208 | 4/1989 | European Pat. Off. |
| 56-25211 | 6/1981 | Japan . |
| 57-026615 | 2/1982 | Japan . |
| 57-026625 | 2/1982 | Japan . |
| 61-233617 | 10/1986 | Japan . |
| WO89/07945 | 9/1989 | PCT Int'l Appl. |
| 2160528 | 12/1985 | United Kingdom . |

OTHER PUBLICATIONS

Howel et al., J. Period. Res., 26(3): 180–183 (1991).
Spirtas et al., Gynecol. Orc., 37:34–38 (1990).
Sacks et al., J. Inf. Dis., 161:692–698 (1990).
Groeneboer et al., Current Eye Res., 8(2):131–138 (1989).
Bohr et al., Arch Dermatol. Res., 279: 147–150 (1987).
Schultz et al., Cornea, 7(2):96–101 (1988).
Schmite & Boggid Hadsen, Actaophtal., 59:422–427 (1981).
Beck et al., Growth Factors, 3:267–275 (1990).
Carpenter & Crowe, Cryobiol., 25:244–255 (1988).
Zatloukal, Ceskoslovenska Farmacie, 39(10): 433–435 (1990) (translated to English).
Preject Product literature in Mar.–Apr. 1992 J. Parenteral Science and Technology (ad.).

*Primary Examiner*—Jeffrey E. Russel
*Attorney, Agent, or Firm*—Janet E. Hasak

[57] ABSTRACT

A formulation for proteins is provided that comprises a lyophilized mixture of a protein, a water-soluble etherified cellulose in an amount that upon reconstitution of the formulation will be sufficient to form a gel, and an excipient to facilitate rehydration of the gel and to maintain protein integrity during storage of the lyophilized gel product. When reconstituted to a gel, this formulation can be applied, for example, to tissue in need of treatment.

13 Claims, 6 Drawing Sheets

RECONSTITUTABLE LYOPHILIZED PROTEIN FORMULATION

BACKGROUND OF THE INVENTION

1. Field of the Invention

This invention is directed to a lyophilized protein formulation, a gel reconstituted from the formulation with water, and a method of topical treatment utilizing the gel.

2. Description of Background and Related Art

In the past ten years, advances in biotechnology have made it possible to produce a variety of proteins using recombinant DNA techniques for pharmaceutical applications. Because of proteolytic degradation in the gastrointestinal tract and poor permeability of these large molecular weight molecules through the intestinal mucosa, oral administration is usually not feasible. Hence, most of these proteinaceous pharmaceutical agents are administered by intravenous, intramuscular, or subcutaneous injections. The parenteral mode of delivery is also desirable for its inherent pulsed administration. Banerjee, P. S., Parenteral Delivery of Peptide and Protein Drugs, in *Peptide and Protein Drug Delivery, Advances in Parenteral Sciences:* 4. Lee V. H. L., ed. (Marcel Dekker, Inc., New York, N.Y., 1991)

Understandably, this form of administration has been poorly accepted by patients, except for those suffering from life-threatening situations. For this reason, some proteins have recently been evaluated for topical applications, including relaxin for inhibition of uterine myometrial contraction and cervical ripening at parturition, tissue factor for clotting blood, TGF-β for wound healing, and interferon-gamma for atopic dermatitis and trauma-related infections.

Methylcellulose is a synthetic derivative of the naturally occurring cellulose polymer. It differs from cellulose in that two of the three hydroxy groups of the glucose unit are substituted by a methoxy group. This group substitution allows cellulose to hydrate and form a hydrogel. In the pharmaceutical industry, this gel has been commonly used for synthetic drugs and small peptides in topical applications. See, e.g., Howell et al., *J. Periodont. Res.*, 26: 180-183 (1991); Spirtos et al., *Gynecol. Oncol.*, 37: 34-38 (1990); Sacks et al., *J. Infect. Dis.*, 161: 692-698 (1990); Groeneboer et al., *Curr. Eye Res.*, 8: 131-138 (1989); Bohr et al., *Arch. Dermatol. Res.*, 279: 147-150 (1987); Schultz et al., *Cornea*, 7: 96-101 (1988); Schmidt et al., *Acta Ophthalmol.*, 59: 422-427 (1981).

In addition, cellulose derivatives have been used to formulate therapeutic proteins or polypeptides for topical use. See, e.g., EP 267,015 published May 11, 1988; EP 308,238 published Mar. 22, 1989; and EP 312,208 published Apr. 19, 1989, which disclose formulation of a polypeptide growth factor having mitogenic activity, such as TGF-β, in a polysaccharide such as methylcellulose; EP 261,599 published Mar. 30, 1988 disclosing human topical applications containing growth factors such as TGF-β; EP 193,917 published Sep. 10, 1986, which discloses a slow-release composition of a carbohydrate polymer such as a cellulose and a protein such as a growth factor; GB Pat. No. 2,160,528 granted Mar. 9, 1988, describing a formulation of a bioactive protein and a polysaccharide; and EP 193,372 published Sep. 3, 1986, disclosing an intranasally applicable powdery pharmaceutical composition containing an active polypeptide, a quaternary ammonium compound, and a lower alkyl ether of cellulose. See also U.S. Pat. No. 4,609,640 issued Sep. 2, 1986 disclosing a therapeutic agent and a water-soluble chelating agent selected from polysaccharides, celluloses, starches, dextroses, polypeptides, and synthetic polymers able to chelate Ca and Mg; and JP 57/026625 published Feb. 12, 1982 disclosing a preparation of a protein and water-soluble polymer such as soluble cellulose. In addition, a method for entrapping enzymes in gel beads for use as a biocatalyst is described in U.S. Pat. No. 3,859,169. Also, a method for preparing polyvinyl alcohol gel intended as a transdermal vehicle for water-soluble synthetic drugs is disclosed in JP 62/205035 published Sep. 9, 1987.

TGF-β is typically formulated at an acidic pH at which it is active. Various methods for its formulation include adding 2-5% methylcellulose to form a gel [Beck et al., *Growth Factors*, 3: 267-275 (1990) reporting the effects on wound healing of TGF-β in 3% methylcellulose], adding collagen to form an ointment or suspension [EP 105,014 published Apr. 4, 1984; EP 243,179 published Oct. 28, 1987; EP 213,776 published Mar. 11, 1987], or adding a cosmetically acceptable vehicle to the TGF-β for a topical formulation [U.S. Pat. No. 5,037,643 issued Aug. 6, 1991].

Additionally, proteins other than TGF-β have been formulated with celluloses for various purposes. For example, epidermal growth factor (EGF) is mixed with a water-soluble cellulose polymer to obtain a sterile aqueous medicinal composition. U.S. Pat. No. 4,717,717 issued Jan. 5, 1988. Also, certain pharmaceuticals are mixed with gelatin, lysozyme, albumin or skim milk along with a hydrophilic polymer such as methylcellulose or hydroxypropyl cellulose to improve their absorption or dissolution rate. JP 57/026615 published Feb. 12, 1982. Moreover, corticosteroids can be formulated with gelatin and methylcellulose or other celluloses to form a non-oil ointment. JP 61/233617 published Oct. 17, 1986. In addition, cellulose derivatives have been used as a gel base for relaxin. WO 89/07945 published Sep. 8, 1989. This publication indicates that the formulated relaxin may be in liquid, frozen, or gel form, or may be lyophilized and reconstituted.

It has also been known to mix an active medicament unstable to heat with a biodegradable protein carrier such as collagen, atelocollagen, or gelatin to form a carrier matrix having sustained-release properties. The resultant mixture is then dried, and the dried material is formed into an appropriate shape, as described in U.S. Pat. No. 4,774,091. Examples of active drugs for this purpose are given as t-PA; prostaglandins; prostacyclines; biohormones, e.g., hGH, bGH, GRF, somatomedins, and calcitonin; interferons; interleukins; tumor necrosis factor; and other cytokines such as macrophage activating factor, migration inhibitory factor, and colony stimulating factor.

The major problem with incorporating proteins into gels is the instability of these proteins in such a configuration. For example, when relaxin is incorporated into the liquid methylcellulose gel medium, the protein is stable at 5° C. for only a month even in the absence of light. In addition, for those proteins such as relaxin and TGF-β, the liquid containing the protein must be mixed with the gel at the time of administration. This is typically accomplished by the cumbersome and time-consuming procedure of intermixing the two components through syringes connected by an interlocking unit. Insufficient mixing may also lead to therapeutic failure.

For example, the current gel formulation package for relaxin contains one protein vial (lyophilized or liquid), one diluent vial (if the protein is in lyophilized form), one liquid gel vial, two syringes, two needles, and one interlock connector for the syringes. In hospitals, physicians are required to undertake a complicated procedure of mixing the protein and wet gel together, reconstituting the protein vial with diluent, withdrawing reconstituted protein solution into one syringe first, and then withdrawing wet gel into another syringe. After removing needles from both syringes, they connect the syringes with an interlock connector and push two syringe plungers back and forth to allow the gel and protein solution to mix for use.

Freeze-drying, or lyophilization, is a process by which the material to be dried is first frozen and then the ice or frozen solvent is removed by sublimation in a vacuum environment. Rey, "Some basic facts about freeze drying," p. xiii, in Goldblith et al., ed., *Freeze Drying and Advanced Food Technology*, Academic Press, London, 1975; Pikal, *Freeze-drying of Proteins*, parts 1 and 2, BioPharm, Sep. 1990, p. 18–27 and Oct. 1990, p. 26–30. An excipient may be added to a formulation to be freeze dried so as to reduce the time for reconstitution. Examples of such agents include a sugar, polyol, amino acid, methylamine, or lyotrophic salt. See, e.g., Carpenter and Crowe, "The Mechanism of Cryoprotection of Proteins by Solutes," *Cryobiology*, 25: 244–255 (1988).

Various small molecular weight drugs have been formulated and then freeze-dried. A dried composition and method of oral administration of drugs, biologicals, nutrients, and foodstuffs is described in U.S. Pat. 5,039,540; however, while the term freeze drying is used, the patent employs a different process entirely. U.S. Pat. No. 4,883,785 discloses a method for preparing a formulation for anti-fungal agent such as amphotericin B, where cyclodextrin is used to improve the solubility of the drug, and lyophilization is employed to preserve the formulation in the solid state.

A freeze-drying method for preparing dry sponge-like polymeric carriers is described in JP 56/25211 published Jun. 24, 1980 by which embedded enzymes (lysozyme, dextranase, mutanase, levanase) can be slowly released when applied to the affected area of the mucous membrane inside the mouth in treating oral cavity and naval cavity diseases.

Moreover, a method is disclosed for preparing lyophilized cellulose lamellae containing low molecular weight molecules, such as pilocarpine chloride, for slow release in the ophthalmic field. Zaloukal, *Ceskoslovenska Farmacie*, 39: 433–435 (1990).

In contrast to small molecular weight drugs, proteins have a high molecular weight associated with extensive secondary, tertiary, and quaternary structure that can be disrupted upon lyophilization. Hence, proteins tend to aggregate and/or deamidate when treated under certain conditions. There is a special need in the art for a topical, water-soluble polysaccharide-based gel formulation of protein that is stable, does not require complicated mixing procedures before application, and rehydrates readily from a powder reconstituted in water.

Accordingly, it is an object of the present invention to provide a topical gel formulation for proteins that is stable for shipping and storage and is easy to prepare prior to administration.

It is another object to provide a lyophilized formulation of protein that does not require a long time for reconstitution.

It is a further object to provide a formulation package having only one product vial (containing lyophilized protein and gel base), one diluent vial, one syringe, and one needle. Such a package provides advantages in product packaging and manufacturing costs.

These and other objects will become apparent to one of ordinary skill in the pharmaceutical, pharmacologic, veterinary, and clinical arts.

SUMMARY OF THE INVENTION

Accordingly, the present invention provides a formulation comprising a lyophilized mixture of a protein, an excipient, and a water-soluble etherified cellulose in an amount that upon reconstitution of the mixture will form a gel. This formulation is suitably reconstituted to a gel with sufficient water.

In another embodiment, the invention provides a method for treating tissue comprising the steps of:

(a) providing a formulation comprising a lyophilized mixture of a protein, an excipient, and a water-soluble etherified cellulose in an amount that upon reconstitution of the mixture will form a gel, (b) reconstituting the mixture in a sufficient amount of water to form a gel, and (c) applying a therapeutically effective amount of the gel topically to the tissue.

In yet another embodiment, the invention provides a method of modulating the reproductive physiology of mammals during pregnancy and parturition comprising administering to the cervix or vagina a therapeutically effective amount of the reconstituted gel formulation containing relaxin as the protein.

In a still further embodiment, the invention supplies a multi-unit formulation package comprising, in one unit, the lyophilized formulation before reconstitution, and in another unit, a diluent (reconstitution agent) for the formulation. Additionally, the formulation may be marketed as a dual-compartment syringe wherein one compartment contains the lyophilized formulation before reconstitution and the other compartment contains a diluent for the formulation.

Thus, the above formulation allows the use of only one product vial, one diluent vial, one syringe, and one needle. Gel preparation only involves reconstitution of the lyophilized material with diluent and withdrawal of the reconstituted gel/protein mixture into a single syringe. This eliminates the need for an interlock connector for the syringes and for gel mixing in the syringes. The advantages in product packaging and field application are obvious.

Lyophilized gel also is convenient for shipping and storage. Some wet gels tend to lose viscosity under light and heat stress, due possibly to a trace impurity in a wet gel that can initiate degradation of gel polymers, which reaction quickly propagates in a liquid environment. Since lyophilized gels are in a solid form, the opportunity for trace impurities to propagate this reaction is minimized.

In addition, lyophilized gel can reduce the manufacturing cost significantly. Lyophilized gels require only one filling operation in which the mixture of protein and gel fluid is filled into a vial for lyophilization. One filling line operation requires much less equipment capital and operating cost than two filling lines required for protein solution in one vial and wet gel in the other.

Furthermore, reconstitution time can be as short as 10 minutes due to the presence of the excipient. Additionally, the effect of lyophilization on the protein is not detrimental to the protein when the formulation is reconstituted.

DESCRIPTION OF THE PREFERRED EMBODIMENTS

The basic components of the gel formulation of this invention are a protein, a water-soluble etherified cellulose, and an excipient. Each of these components is addressed more fully below.

By "protein" is meant a sequence of amino acids for which the chain length is sufficient to product the higher levels of tertiary and/or quaternary structure. This is to distinguish from "peptides" or other small molecular weight drugs that do not have such structure. Typically, the protein herein will have a molecular weight of at least about 15-20 kD, preferably at least about 20 kD.

Examples of proteins encompassed within the definition herein include mammalian proteins, such as, e.g., a growth hormone, including human growth hormone, des-N-methionyl human growth hormone, and bovine growth hormone; parathyroid hormone; thyroid stimulating hormone; thyroxine; lipoproteins; $\alpha$1-antitrypsin; insulin A-chain; insulin B-chain; proinsulin; follicle stimulating hormone; calcitonin; leutinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor; receptors for hormones or growth factors; integrin; thrombopoietin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-$\beta$; platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\gamma$5; insulin-like growth factor-I and -II (IGF-I and IGF-II); insulin-like growth factor binding proteins; CD proteins such as CD-3, CD-4, CD-8, and CD-19; erythropoietin; osteoinductive factors; a bone morphogenetic protein (BMP); somatotropins; an interferon such as interferon-alpha, -beta, and -gamma (IFN-$\alpha$, -$\beta$, and -$\gamma$); colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides. Preferred proteins herein are therapeutic proteins when applied topically, particularly those having a therapeutic effect when applied topically to treat tissue. These include growth factors such as TGF-$\beta$, TGF-$\alpha$, PDGF, EGF, FGF, and IGF-I, plasminogen activators such as t-PA, clotting factors such as tissue factor and factor VIII, hormones such as relaxin and insulin, or cytokines such as IFN-$\gamma$, most preferably tissue factor, relaxin, and TGF-$\gamma$.

"IFN-$\gamma$" is meant to include IFN-$\gamma$ in a mature, pro, met, or des(1-3) (also referred to as desCysTyrCys IFN-$\gamma$) form, whether obtained from natural sources, chemically synthesized, or produced by techniques of recombinant DNA technology. A complete description of the preparation of recombinant human IFN-$\gamma$, including its cDNA and amino acid sequences, is provided in U.S. Pat. Nos. 4,762,791; 4,929,544; 4,727,138; and 4,925,793. CysTyrCys-lacking recombinant human IFN-$\gamma$ interferons, including variously truncated derivatives, are disclosed, for example, in EP 146,354. Non-human animal IFN-$\gamma$ is, for example, disclosed in EP 88,622. The term includes variously glycosylated forms and other variants and derivatives of such interferons, whether they are known in the art or will become available in the future. Examples of such variants include alleles and the products of site-directed mutagenesis in which residues are deleted, inserted, and/or substituted (see, e.g., EP 146,354).

By "TGF-β" is meant the family of molecules that have either the full-length, native amino acid sequence of any of the TGF-βs from any species, including the latent forms and associated or unassociated complex of precursor and mature TGF-β ("latent TGF-β"). Reference to such TGF-β herein will be understood to be a reference to any one of the currently identified forms, including TGF-β1, TGF-β2, TGF-β3, TGF-β4, and TGF-β5 and latent versions thereof, as well as to TGF-β species identified in the future, including members of the TGF-β family. Members of the TGF-β family are defined for purposes herein as those which have nine cysteine residues in the mature portion of the molecule, share at least 70% homology, preferably at least 80% homology, with other known TGF-β sequences in the mature region, and compete for the same receptor. In addition, they all appear to be encoded as a larger precursor that shares a region of high homology near the N-terminus and shows conservation of three cysteine residues in the portion of the precursor that will later be removed by processing. Moreover, the TGF-βs appear to have a four or five amino acid processing site. The TGF-β is appropriately from any source, preferably mammalian, and most preferably human for treating humans. TGF-β from animals other than humans, for example, porcine or bovine sources, can be used for treating humans. Likewise, if it is desirable to treat other mammalian species such as domestic, farm, zoo, sports, or pet animals, human TGF-β, as well as TGF-β from other species, is suitably employed.

"Relaxin" denotes a functional protein having specific hormonal functions, such as, for example, the modulation of the reproductive physiology of human beings and possibly other mammals, including, but not limited to, maintaining pregnancy, effecting parturition, and enhancing sperm motility as an aid in fertilization. Human relaxin and its methods of preparation, including synthesis in recombinant cell culture, are known. EP 101,309 and 112,149. In addition, relaxin may be prepared by synthesis of the A and B chains, and purification and assembly thereof, as described in EP 251,615 published Jan. 7, 1988. The term includes relaxins from native or recombinant sources as well as relaxin variants, e.g., those with insertions, substitutions, or deletions of one or more amino acid residues, glycosylation variants, the prepro- and pro- forms, etc. These variants include those having 33 amino acids in the B chain rather than the 29 found in the natural molecule. The preferred relaxin herein is human relaxin.

"Tissue factor" refers to a protein capable of correcting various bleeding disorders, e.g., by inducing coagulation, particularly those disorders associated with coagulation factor deficiencies. Included within this term is human tissue factor protein having native glycosylation and the amino acid sequence set forth in FIG. 2 of EP 278,776 published Aug. 17, 1988, analogous tissue factor proteins from other animal species such as bovine, porcine, ovine, and the like, deglycosylated or unglycosylated derivatives of such tissue factor proteins, and biologically active amino acid sequence variants of tissue factor, including alleles and in vitro-generated covalent derivatives of tissue factor proteins that demonstrate at least one of its activities. The preferred tissue factor herein is human tissue factor.

The "water-soluble etherified cellulose" herein is a cellulose ether polysaccharide that constitutes the gelling agent for the protein formulation herein. The term "water soluble" as applied to the etherified cellulose herein is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient.

Examples of etherified cellulose herein include alkyl celluloses, hydroxyalkyl celluloses, and alkylhydroxyalkyl celluloses, for example, methylcellulose, hydroxyethyl cellulose, hydroxypropyl methylcellulose, and hydroxypropyl cellulose. The preferred gelling agent herein is one that is inert to biological systems, non-ionic, non-toxic, simple to prepare, and not very runny or viscous, will not destabilize the protein held within it, and allows good rehydration of lyophilized gel. It is noted that the preferred cellulose derivatives herein are those that are not anionic, such as those in the form of alkali metal salts, e.g., Li, Na, K, or Cs salts, or carboxymethyl cellulose, to avoid any inactivation of the protein, particularly for TGF-β.

Preferably the etherified cellulose is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred are those cellulose derivatives with highly polar substituted side chains, which show better rehydration properties than non-polar forms such as methylcellulose. The most preferred cellulose herein is hydroxyethyl cellulose due to its shorter reconstitution time as well as its ease of preparation and sterilization by autoclaving.

An "excipient" is an agent whose principal function is the acceleration of reconstitution of the lyophilized mixture (i.e., it reduces gel rehydration time). A secondary function of the excipient is its ability to stabilize the protein, i.e., it maintains or improves protein stability. In a polymer solution, the flexible chains of dissolved macromolecules interpenetrate and entangle because of the constant Brownian motion of their segments. In an aqueous solution, the functional groups of each chain are encased in a solvating sheath of hydrogen-bonded water molecules. This envelope of water of hydration prevents neighboring chain segments from forming interchain hydrogen bonds.

Without being limited to any one theory, it is believed that when this water is removed during lyophilization, the polymer molecules are now free to associate and form hydrogen and/or hydrophobic bonds that may be irreversible, or at the very least, only slowly reversible upon subsequent rehydration. This would explain why lyophilized methylcellulose gels take up to two days to rehydrate. Certain excipients preferentially hydrate other macromolecules in aqueous solutions and in the solid state as well. In addition, lyophilization of methylcellulose gels containing such excipients requires lower operating shelf temperatures as well as extended drying times. The resulting cakes also exhibit lower collapse temperatures and higher final moisture contents. These are all indications of stronger interaction between water and cellulose molecules. The rehydration of these cakes takes about two hours versus two days for samples not containing the excipient. By maintaining the hydration sheath throughout the drying process, most of the interchain bonding seems to be eliminated, so that the gel can rehydrate fully and quickly.

The particular excipient used for this purpose will depend on the specific protein being formulated, but preferably is a sugar such as sucrose, an amino acid such as monosodium glutamate, a methylamine such as betaine, a lyotrophic salt such as magnesium sulfate, or a polyol such as trihydric or higher sugar alcohols, most preferably glycerin, erythritol, glycerol, arabitol, xylitol, sorbitol, and mannitol, as well as propylene glycol. See, e.g., Carpenter and Crowe, supra. The preferred excipient herein is one that reduces the rehydration time of the lyophilized mixture to less than 30 minutes (i.e., is clinically viable) without adversely affecting the stability of the protein. For relaxin and TGF-$\beta$, the excipient of choice is sucrose, whereas for tissue factor, the preferred excipient is glycerol.

Additional additives may be added to the formulation as desired for imparting certain other properties, including a co-solvent, anti-oxidant, or agent to enhance absorption of the protein by the tissue. For example, relaxin may be formulated with an anti-oxidant such as methionine (e.g., in amounts of about 0.01 to 0.1% w/v of the gel) or ascorbic acid (about 0.3–1% w/v of the gel), or with a co-solvent such as glycerol (about 0.1–20% w/v of the gel), and/or ethanol (about 0.1–20% w/v of the gel) to minimize oxidation of the protein by light. These agents can be used alone or in a combination thereof, preferably in an amount of about 1 to 25% by weight, preferably 2 to 10% by weight, of the gel, taking into account the amounts of the other ingredients. The preferred of these agents for relaxin is glycerol or ethanol, in an amount of 0.1 to 10% (w/v) of the gel.

Examples of agents to enhance absorption (as by the cervix or vagina if the protein is relaxin) include molecules with a structure similar to that of cholesterol, such as glycocholate, e.g., sodium glycocholate, cholate, e.g., sodium cholate, and fusidic acid and its derivatives, including salts and esters such as 24,25-tourodihydrofusidate, non-ionic surfactants, derivatives of fatty acids having about 7 to 25 carbon atoms, such as oleic acid, niacinamide, nicotinic or salicyclic acid, or their salts or esters, and azone.

The formulation herein also may suitably contain more than one protein as necessary for the particular indication being treated, preferably those with complementary activities that do not adversely affect the other protein. For example, those proteins with mitogenic or angiogenic activity include, e.g., TGF-$\beta$, IGF-I or -II, TGF-$\alpha$, human growth hormone, EGF, vascular endothelial growth factor, vaccinia virus growth factor, acidic or basic FGF, angiogenin, NGF, PDGF, human endothelial cell growth factor, or fibronectin. Such proteins are suitably present in combination in amounts that are effective for the purpose intended.

The respective amounts of the various required components in the formulation, and the preferred amounts, are indicated below.

The protein formulations herein will be dosed in a fashion consistent with good medical practice taking into account the nature of the tissue to be treated, the type of protein, the indication to be treated, the species of the host, the medical condition of the individual patient, the presence of any other co-treatment drug in the composition, the site of delivery of the protein, the scheduling of administration, and other factors known to practitioners. Because of differences in host response, significant site-to-site and patient-to-patient variability exists. For purposes herein, the "therapeutically effective amount" of protein or gel is an amount that is effective to treat soft or hard tissue for the intended purpose of the protein at the desired site.

As a general proposition, depending on the protein type, the protein is formulated at an amount of about 0.010 $\mu$g/ml–5 mg/ml, preferably about 0.2 to 1 mg/ml, of the gel (wet gel, before lyophilization). If the protein is TGF-$\beta$, preferably, the amount is about 0.025 $\mu$g per ml to 1 mg per ml of gel, most preferably about 0.2–1 mg per ml of gel. If the protein is relaxin, the preferred amount is about 0.1 to 1 mg/ml of gel. If the protein is tissue factor, the preferred amount is about 0.2 to 1 mg/ml of gel, and the preferred dose is about 1–25 $\mu$g/kg. If the protein is IFN-$\beta$, the preferred dose is about 0.01 mg/M$^2$ to 0.1 mg/M$^2$ per day for atopic dermatitis.

As noted above, these suggested amounts of protein are subject to a great deal of therapeutic discretion. The key factor in selecting an appropriate dose is the result obtained, for which veterinary or clinical parameters are used to determine an indication-appropriate endpoint. For example, the formulation herein is useful in the treatment of soft or hard tissue, generally in mammals and preferably humans, preferably not ocular tissue, and preferably skin or bone. For TGF-$\beta$ this would include the promotion of surface wound healing, and the topical application to internal surgical incisions. Examples of such applications include treatment of burns; surface ulcers, including decubital, diabetic, dental, hemophiliac, and varicose ulcers; wounds, including lacerations, incisions, and penetrations; surgical incisions, including those of cosmetic surgery; and bony defects or repair. For relaxin, these indications include cervical ripening at parturition and inhibition of uterine myometrial contraction. For t-PA, this treatment would include healing of adhesions. For IFN-$\beta$, these indications include atopic dermatitis, other rashes, and trauma-related infections that can be treated topically. For tissue factor, this treatment includes hemostat application to stop bleeding. The measurements of veterinary and clinical parameters for these indications are well known to those veterinarians, clinicians, and pharmacologists skilled in the art.

The cellulose derivative must be present in the formulation in sufficient quantities that a gel of the proper viscosity will be formed upon reconstitution for topical application. The amount of etherified cellulose employed will depend mainly on the molecular weight and the viscosity of the particular etherified cellulose being employed. In general, the higher the viscosity and molecular weight of the cellulose derivative, the lower the amount needed in the gel. The lower amount of such derivative is generally about 1% (w/v) of the gel (before lyophilization of the mixture) for higher viscosity derivatives, and the upper limit of such amount is determined by the maximum amount of low-viscosity or low-molecular-weight etherified cellulose that can be added to the formulation that will still maintain the effectiveness of the gel. The cellulose derivative is preferably present in the gel formulation in the range of about 1–20% (w/v) of the gel, depending on the viscosity and molecular weight, more preferably about 1–15%, and most preferably about 2–10% of the gel. If the etherified cellulose is a high-viscosity derivative (e.g., methylcellulose of the A4M Type from Dow Chemical or hydroxyethyl cellulose under the tradename Natrosol), then the preferred range is about 2–5%

(w/v) of the gel, and most preferably about 3-4% (w/v).

The concentration of excipient will depend mainly on the type of excipient and protein employed. If sugar is the excipient, it is preferably present in amounts of about 0.1 to 2M of the gel (before lyophilization of the mixture), and if glycerol is the excipient, it is preferably present in amounts of about 0.5 to 5% (w/v) of the gel, more preferably about 1-4% (w/v). The determination of the amount to employ is made by examining cake appearance, stability, and reconstitution time.

The particularly preferred formulations herein, based on volume of total gel before lyophilization, are presented below. The preferred relaxin formulation is about 0.2-0.5 mg/ml, preferably about 0.2 mg/ml, relaxin, about 3-4% (w/v), preferably about 3.5% (w/v), hydroxyethyl cellulose, and about 0.2-0.6M, preferably about 0.2M, sucrose, optionally with about 0.03-0.1% (w/v), preferably about 0.05% (w/v), free methionine. The preferred TGF-$\beta$ formulation herein is about 0.2-1 mg/ml, preferably about 0.5% mg/ml, TGF-$\beta$, about 3-4% (w/v), preferably about 3.5% (w/v), hydroxyethyl cellulose, and about 0.2-0.6M, preferably about 0.2M, sucrose. The preferred tissue factor formulation herein is about 0.5-1 mg/ml, preferably about 1 mg/ml, tissue factor, about 3-4% (w/v), preferably about 3.5% (w/v), hydroxyethyl cellulose, and about 1-4% (w/v), preferably about 1% (w/v), glycerol.

The formulation herein is preferably sterile. Sterility of the protein is readily accomplished by sterile filtration of the protein in the buffer through (e.g., 0.2 micron) membranes prior to mixing with the other ingredients. The protein ordinarily will be stored as an aqueous solution prior to formulation and lyophilization, although lyophilized formulations of the protein for reconstitution prior to admixture with the etherified cellulose are also acceptable.

Sterility of the entire mixture is accomplished in one procedure by autoclaving the ingredients except for protein at about 120° C. for about 30 minutes and storing the resulting mixture at 5° C. for about 24 hours to allow the etherified cellulose to hydrate before mixing with the sterile-filtered protein solution. Then the two mixtures are combined and lyophilized for final formulation.

The active protein ingredient is generally combined at ambient temperature at the appropriate pH, and at the desired degree of purity, with the other ingredients. The pH of the formulation will depend mainly on the type of protein being formulated. In certain instances, as with TGF-$\beta$, relaxin, and IGF-I, the protein is generally formulated at an acidic pH, i.e., less than pH 7, preferably about pH 3-6.5, and more preferably about pH 4-6.

Further, if the protein to be administered is TGF-$\beta$, to be effective, it is converted by the body to its activated form, i.e., the mature form is cleaved from its precursor using a suitable enzyme and the resultant complex is treated with acid or other appropriate agent, to activate the TGF-$\beta$. Nevertheless, TGF-$\beta$ is suitably administered in an inactive or delayed release form such as a complex of mature TGF-$\beta$ with proTGF-$\beta$ not containing mature TGF-$\beta$ (i.e., the remaining precursor of TGF-$\beta$), with a TGF-$\beta$ binding protein, or with alpha$_2$-macroglobulin. The latent form is then converted to the active form either by naturally occurring mechanisms in the local environment or by formulation with TGF-$\beta$ activating agents described above. See, e.g., Gentry et al., *Mol. Cell. Biol.*, 4162-4168 (1988); Miyazono et al., *J. Biol. Chem.*, 263: 6407-6415 (1988); Wakefield et al., *J. Biol. Chem.*, 263: 7646-7654 (1988); Keski-Oja et al., *J. Cell Biochem. Suppl.*, 11A: 60 (1987); Kryceve-Martinerie et al., *Int. J. Cancer*, 35:553-558 (1985); Lawrence et al., *Biochem. Biophys. Res. Commun.*, 133: 1026-10134 (1985); Lawrence et al., *J. Cell Physiol.*, 121: 184-188 (1984). Thus, the pH of the TGF-$\beta$ composition may suitably reflect the conditions necessary for activation.

After the protein, etherified cellulose, and excipient are mixed together, the formulation is lyophilized. This may be accomplished by any suitable means, including ramping the temperature of the sample down to a temperature suitable for primary drying. This temperature is determined by the glass transition temperature of the formulated cellulose gel without protein using resistivity measurements. Typically, the primary drying temperature will range from about $-30°$ to $-60°$ C. at a suitable pressure, ranging typically from about 130 to 170 $\mu$m, preferably about 150 $\mu$m. The size and type of the container holding the sample (e.g., cuvette or vial) will mainly dictate the time required for drying, which generally ranges from about 1 to 7 days.

A secondary drying stage is then typically carried out at about 5°-20° C., depending primarily on the type and size of container 10 and the type of protein employed. The time and pressure required for secondary drying will be that which produces a suitable lyophilized cake, dependent, e.g., on the temperature and other parameters. Typically, the time will take at least about 4 hours and the pressure will be the same as that employed during the primary drying step.

At the desired stage, typically in a clinical setting when it is desired that the gel be applied to the patient, the lyophilized powder is reconstituted with sufficent diluent to rehydrate the gel for topical application. Reconstitution generally takes place at a temperature of about 5°-10° C. to ensure complete hydration, although other temperatures may be employed as desired. The time required for reconstitution will depend, e.g., on the type of excipient and protein. The diluent employed for this purpose is typically an aqueous medium such as water, water for injection, Ringer's solution, or buffer.

The diluent is suitably contained in a separate vial in a pre-packaged kit that also contains a vial of the lyophilized formulation. Alternatively, the lyophilized mixture is suitably packaged in one compartment of a dual-chamber syringe, and the other compartment is filled with the diluent. An example of a dual-compartment syringe suitable for this purpose is that marketed by Preject Inc., Warwick, R.I.

The invention will be more fully understood by reference to the following examples. They should not, however, be construed as limiting the scope of the invention. All literature citations are incorporated by reference.

EXAMPLES

The protocols and methods described below were employed in the examples that follow:

A. Gel Preparation

1. Hydroxyethylcellulose (Natrosol)

The appropriate amount of water or a desired buffer was added to a measured amount of Natrosol powder, either Natrosol 250 MR or Natrosol 250 HR. The solution was then stirred at room temperature for at least four hours at medium speed until the solution gelled. The concentration of the gel was 1% (w/v) and 3.5% (w/v) for reconstitution and stability studies, respectively.

2. Methylcellulose or Hydroxypropyl Methylcellulose (Metolose)

The buffer was heated in a tissue culture flask while stirring. The heat was turned off once the temperature had reached 85° C. Metolose USP powder (Metolose SM-4000 or Metolose 90SH-4000) was then dispersed into the hot solution. The flask was capped with a double-headed filter unit and autoclaved using the liquid cycle. After autoclaving, the double-headed filter unit was taken off in the laminar flow hood and a regular cap was put on. The gel was then stirred at 5° C. overnight and wrapped in foil the next day.

3. Hydroxypropylcellulose (Klucel HF)

An amount of water at least six times the dry weight of Klucel powder was heated to 55° C. The dry Klucel powder was added to the hot water while stirring. Continuous stirring was maintained for 15 minutes to ensure uniform dispersion. Enough cold water was then added to make the desired concentration. Stirring was continued at a slow speed until gelation occurred.

B. Viscosity

Gel viscosity was measured with a Brookfield viscometer. Half a milliliter of the gel was placed in the sample cup with spindle CP-51. After equilibrating at 25° C. at the lowest rpm for 5 minutes, torque measurements of spindle were collected and calculated to obtain viscosity. The viscometer rotation was changed every 15 seconds in a stepwise manner from 0.5 rpm to 100 rpm and then back down to 0.5 rpm.

C. Autoclave

Approximately 10 ml of each of the gels we re autoclaved in 50 ml beakers at 121° C. for 30 minutes using the liquid cycle in the Getinge PACS 50 autoclave.

D. Eutectic Temperature Determination

Figure 1:
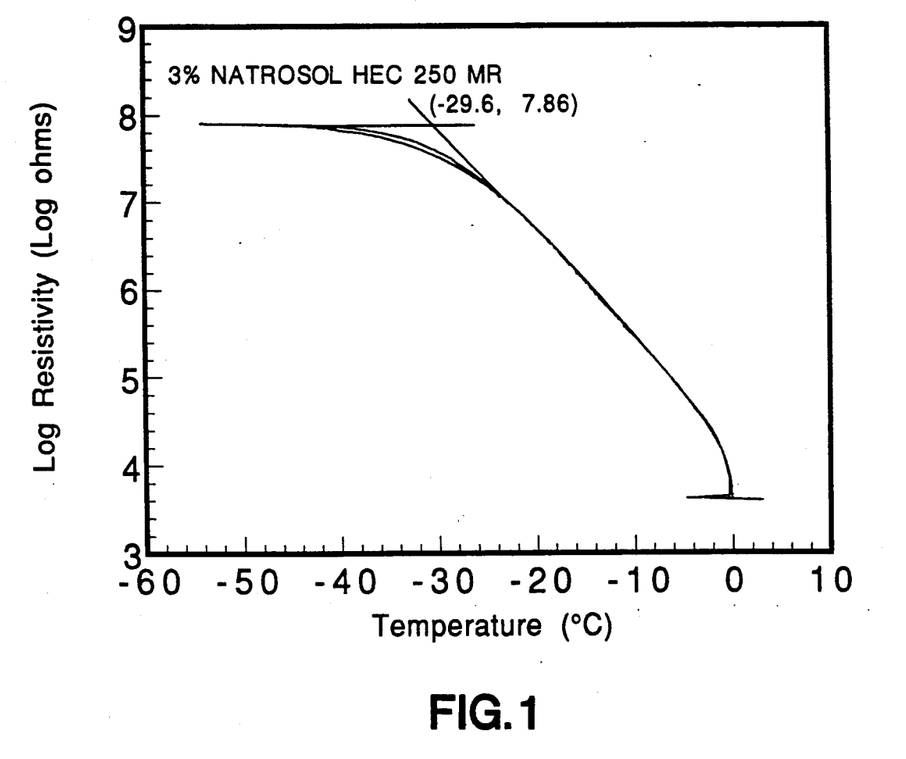
FIG. 1 illustrates a graph of log resistivity versus temperature and how glass transition temperature is determined from resistivity for a 3% (w/v) hydroxyethyl cellulose gel so as to obtain primary drying temperature for gel lyophilization.

The primary drying temperature was based on the glass transition temperature of the formulated gel without protein as determined by resistivity measurements. An Ultra-Vu disposable cuvette was filled with just enough gel to cover the resistivity probe, and the whole assembly was placed in the Planer Biomed incubator. After equilibration at 5° C. for 10 minutes, the sample was cooled at 5° C. per minute to −60° C. The sample was again equilibrated at this temperature for 15 minutes before it was warmed at 2° per minute to 20° C. The glass transition temperature was determined as shown in FIG. 1. This temperature is about −30° C. for a 3% (w/v) Natrosol 250 MR gel prepared in 10 mM citrate without salt at pH 5.0.

E. Lyophilization

The general scheme for the lyophilization cycle was as follows:
Cool the lyophilizer to 5° C. in 15 minutes.
Keep the samples at 5° C. for 30 minutes.
Freeze in 2 hours to −55° C.
Hold samples at −55° C. for a minimum of two hours.
Ramp up to −30° C. in 2 hours for primary drying.
Conduct primary drying at −30° C. at a pressure of 150 μm.

The betaine samples were frozen in a −70° C. freezer overnight and transferred to the lyophilizer only after the shelves had reached −55° C. This procedure was necessary to prevent collapse of these samples during primary drying.

The duration of primary drying depended on whether cuvettes or vials were used. If cuvettes were used, primary drying required up to 5 to 6 days, whereas if vials were used, less than two days were needed.

Conduct secondary drying at either 20° C. (cuvettes) or 5° C. (vials) for at least 4 hours at the same pressure. Vials were heated only to 5° C. so that they would be at the same temperature as the controls used in the stability studies.

If the vials contained active materials, then upon conclusion of the lyophilization run, the vials were subjected to a ultra-high-purity-grade nitrogen gas atmosphere before sealing.

F. Cuvette Fill

The gels containing different excipients were filled from a syringe with an 18-gauge needle into the disposable cuvettes until they were just above the narrowest part of the cuvette (approximately 1 g of gel). Five cuvettes of each excipient were filled. The weights of the empty and filled cuvettes were recorded. The cuvettes were then arranged into small groups and placed on the middle shelf of the lyophilizer.

G. Reconstitution of Cuvettes

The lyophilized gel in its cuvette was weighed and the difference from the weight of the cuvette filled with non-lyophilized gel was noted. It was assumed that the loss in weight was solely due to sublimation. This loss was then replaced with the same volume of water to reconstitute the lyophilized gel to its original concentration. The water was added slowly along the side of the cuvette to minimize bubble formation.

H. Reconstitution Time Determination

Figure 2:
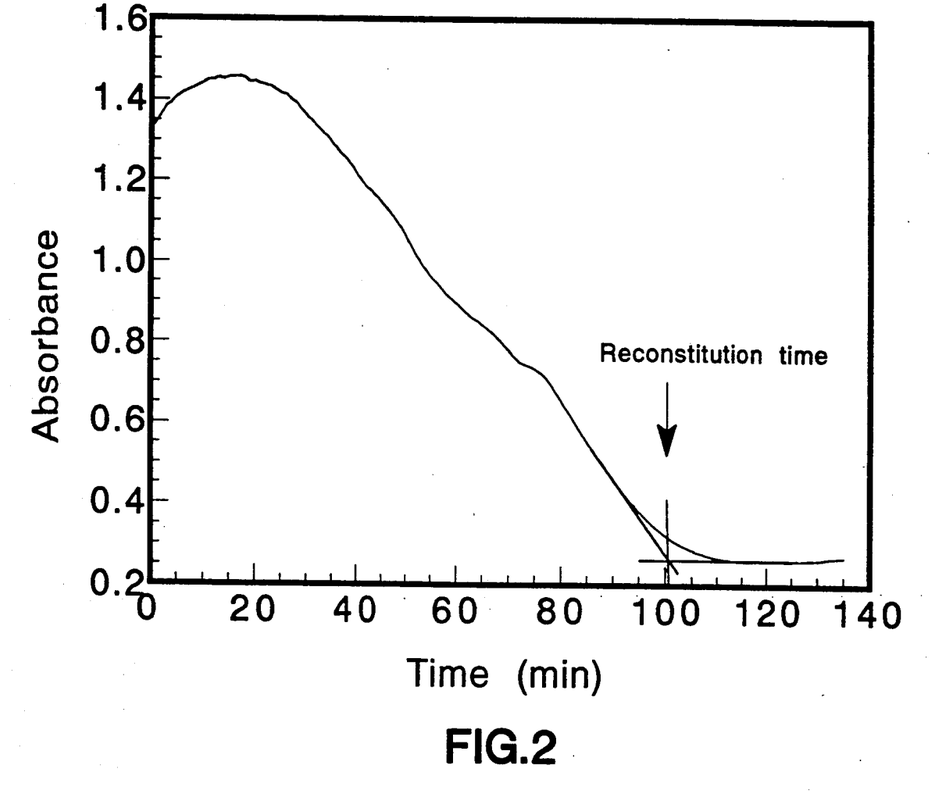
FIG. 2 illustrates a graph of ultraviolet absorbance versus time for a 1% (w/v) hydroxyethyl cellulose gel containing 5 mM polyethylene glycol (PEG) 1000 so as to determine reconstitution time for lyophilized gel.

The uv absorbance of the reconstituted gel at 340 nm was measured over time using the Hewlett-Packard spectrophotometer. The spectrophotometer was zeroed against water as a reference solvent. Absorbance was measured immediately after water was added to the lyophilized gel and measurements were taken thereafter at one-minute intervals. A two-hour time frame was usually allotted to ensure complete reconstitution of the lyophilized gel. Reconstitution was judged to be complete when the absorbance readings leveled off. The reconstitution time was then determined as shown in FIG. 2.

I. Protein Preparation

Depending on the status of the protein (i.e., concentration and buffer system), preparation may or may not be necessary. If the protein concentration was too low, then the bulk solution was concentrated with an Amicon Stirred Cell to more than 10 times the required concentration for HPLC assays with a 10K molecular weight cut-off filter. Protein concentration was measured with the spectrophotometer over the range of 240 to 400 nm. If the buffer system was not appropriate, then the bulk solution was dialyzed against the desired buffer system at 5° C. for about 24 hours.

J. Gel Preparation and Vial Fill

Excipients, hydroxyethyl cellulose powder, and protein were combined with water to make a 3.5% (w/v) cellulose solution. The solutions were then stirred at room temperature for at least 4 hours at medium speed until the solutions gelled. The gels were filled with a 18½ gauge syringe into 3-cc vials. Approximately 0.5 g of the gels were filled into each vial. The weights of the empty and filled vials were recorded.

K. Stability Schedule

Two vials per time point were set up for each stability study. Time points were at one-week intervals. After Time 0 the vials were divided into two groups that were stored at 5° C. and 30° C., respectively.

L. Reconstitution and Dilution for HPLC Study

The same reconstitution procedure as the one for cuvette reconstitution was followed. The gels were reconstituted at 5° C. overnight to ensure complete rehydration. The reconstituted gels were then diluted 10 times the next day with the appropriate buffer for the intended HPLC assay. The diluted gels were vortexed at a setting of 10 on the Vortex Mixer for at least 2 minutes to ensure that the gel was completely dissolved.

EXAMPLE I

This example illustrates the invention using relaxin as the protein.

A. Reverse-Phase HPLC Assay for Relaxin

Instrument: HP 1090
Column: Vydac C4
Mobile Phase: A) 0.1% trifluoroacetic acid (TFA) in water, B) 0.1% TFA/90% acetonitrile
Gradient: 20% to 50% B in 30 minutes
Flow Rate: 1.0 ml/min
Injection Volume: 100 μl
Protein Concentration: 20 μg/ml
UV Detector: 214 nm
Run Time: 37 min.
Post Time: 15 min.
Temperature: Ambient

B. Relaxin ELISA

This assay determines the concentration of intact relaxin. The liquid relaxin and the lyophilized gel were diluted with relaxin diluent (phosphate buffered saline, 0.5% bovine serum albumin, 0.05% polysorbate, 0.01% thimerosal) to 5 ng/ml, 2.5 ng/ml, and 1.25 ng/ml. Duplicate aliquots of the diluted samples were submitted for analysis using antibodies to relaxin.

C. Study No. 1: Effects of Different Grades of PEG and Glycerol on Reconstitution Time of the Gel Previous studies have shown that polyethylene glycol (PEG) 300 shortens reconstitution time. This study further explores this phenomenon using different grades and concentrations of PEG as well as glycerol. The major route of relaxin degradation in methylcellulose gel has been found to be through oxidation of methionine. To reduce this possibility, 0.05% (w/v) free methionine was included in all the relaxin formulations prepared hereafter. The combination of methionine and glycerol was found to be protective against relaxin degradation, so these components were first tested in the 1% w/v hydroxyethyl cellulose gel. A 1% w/v gel was made because gels with higher concentrations often had trapped bubbles that would interfere with absorbance measurements. The excipients included in this study were:
1) glycerol: 0.1% w/v, 1% w/v, 5% w/v, 10% w/v
2) PEG 300: 5 mM, 10 mM, 25 mM,
3) PEG 600: 5 mM, 10 mM, 25 mM
4) PEG 1000: 5 mM, 10 mM, 25 mM
PEG 3350: 5 mM, 10 mM, 25 mM

D. Study No. 2: Effects of Different Classes of Excipients on Reconstitution Time of the Gel This study was initiated to test the different classes of excipients that have been shown to be stabilizers for proteins. The classes of excipients and their representatives tested in this study were:
1) Sugars - sucrose
2) Polyols - mannitol
3) amino acids - monosodium glutamate (MSG)
4) methylamines - betaine
5) Lyotrophic salts - magnesium sulfate The concentrations prepared for each excipient were 0.2M, 0.4 M, 0.6M, 0.8M, 1.0M, 1.5M, and 2.0 M. These concentrations were chosen because Carpenter and Crowe, supra, found that for these excipients the optimal solute concentration for protein protection was between 0.2 and 1.8M.

E. Study No. 3: Effects of PEG. Glycerol, and Sucrose on Gel Containing Relaxin Synthetic human (H2) relaxin [Johnston et al., in *Peptides: Structure and Function,* Deber, C. M., et al. (eds.), p. 683-686, Pierce Chemical Company, Rockford, Ill., 1985] was employed. This product is currently available from Genentech, Inc., South San Francisco, Calif., to clinical investigators for clinical trials. The excipients selected were 1% w/v glycerol and 50 mM PEG 300. The concentration of 1% w/v of glycerol was found in earlier studies to give a good lyophilized cake, and the concentration of 50 mM PEG 300 was chosen because it was expected to give a reasonable reconstitution time. The sucrose concentration used was 0.2M. All gels contained 0.2 mg/ml of protein. Primary drying was carried out at −40° C. for 56 hours and 30 minutes. Again, a three-week stability study was set up. Reverse-phase HPLC of reconstituted gel was used to monitor protein stability.

F. Results

1. Gel Selection

Figure 3:
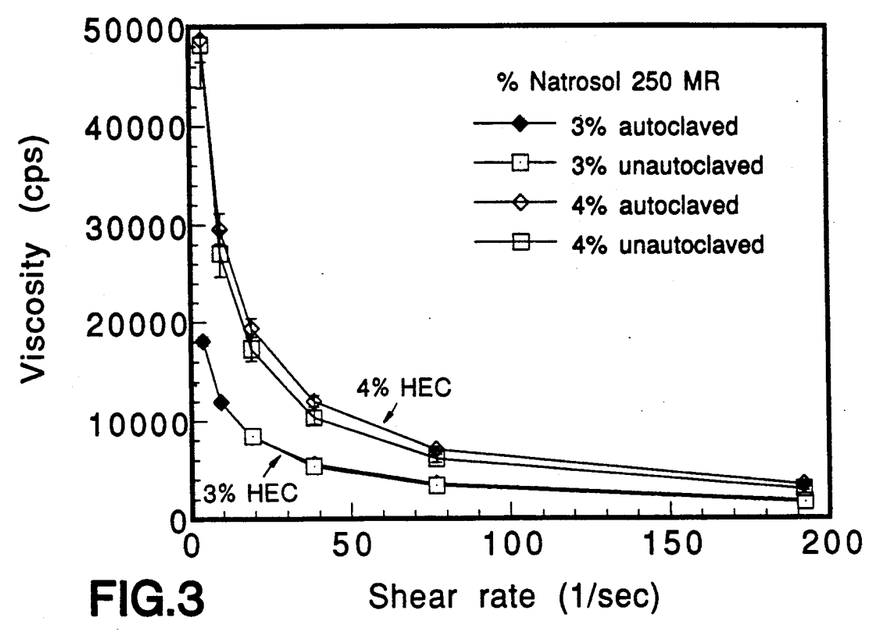
FIG. 3 illustrates a graph of viscosity versus shear rate to show the effect of the autoclave on the viscosity of 3% and 4% (w/v) hydroxyethyl cellulose (HEC) gels.

Of the five gels examined (Natrosol 250 MR, Natrosol HR, Metolose SM4000, Metolose 90SH4000, and Klucel), only the two grades of Natrosol gels survived autoclaving. Viscosity was measured to confirm that there was no degradation after autoclaving (FIG. 3). The MR grade was chosen because it can be prepared at the concentration that would provide the desired viscosity.

2. Viscosity

Figure 4:
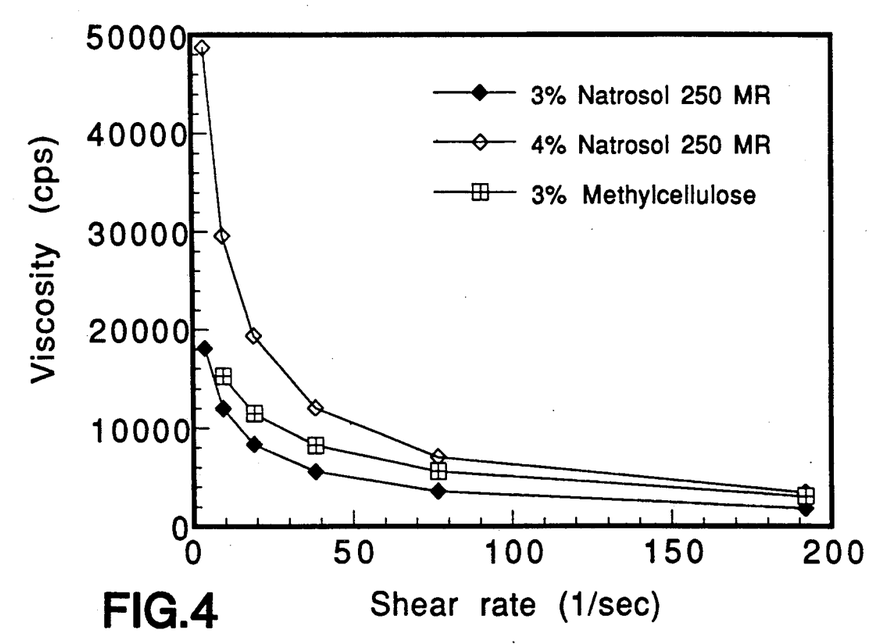
FIG. 4 illustrates a graph of viscosity versus shear rate to determine the concentration of hydroxyethyl cellulose (HEC) gel that would give the same viscosity as a 3% (w/v) methylcellulose (MC) gel.

Since the present study was based on the relaxin gel project, many parameters were kept constant to reduce undesired variabilities in the experiment. Viscosity of the gel was kept constant by adjusting cellulose concentration. From viscosity measurements the Natrosol gel concentration corresponding to the 3% (w/v) methylcellulose gel was found to be 3.5% (w/v) (FIG. 4).

3. Study No. 1

Figure 5:
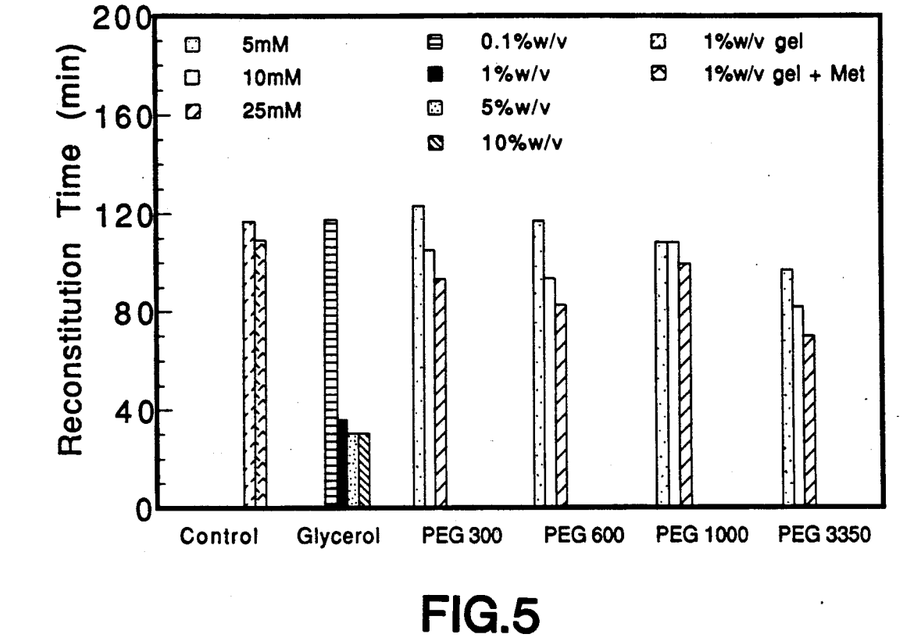
FIG. 5 depicts the reconstitution times of 1% (w/v) hydroxyethyl cellulose gels containing differing concentrations of glycerol or different grades of PEG as excipients as determined by uv absorbance. The control is the hydroxyethyl cellulose gel alone or the gel with methionine.

Both the glycerol- and PEG-containing cakes were yellow after lyophilization. All samples gave good cakes except for the gels containing 5% (w/v) glycerol or greater. However, the higher concentrations of glycerol required the shortest reconstitution time. As for PEG, the higher the molecular weight and/or higher the concentration, the shorter the reconstitution time (FIG. 5). The results suggest that a glycerol concentration greater than or equal to 1% w/v reduced the reconstitution time significantly.

4. Study No. 2

Figure 6:
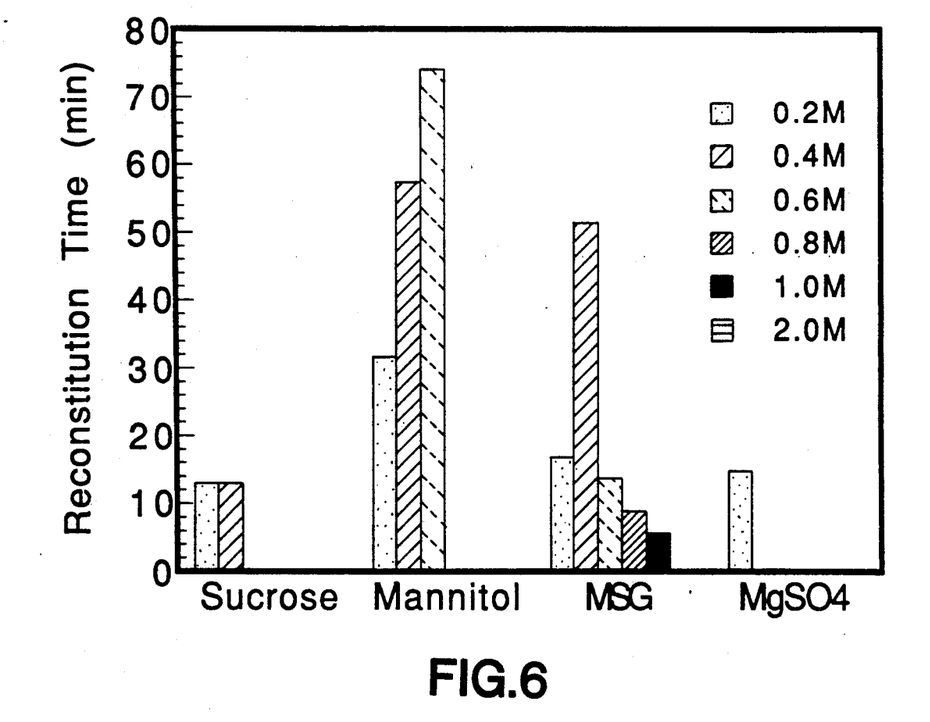
FIG. 6 depicts the reconstitution times of 3.5% (w/v) hydroxyethyl cellulose gels containing four different excipients in a range of concentrations.

It was found from resistivity measurements that a solution of 2.0M betaine would not crystallize until it had reached a temperature of $-70°$ C. Therefore, the betaine samples were frozen in a $-80°$ C. freezer before transferring to the lyophilizer. As for the other excipients at higher concentrations, those listed below were insoluble, so they were not prepared for lyophilization:
1) sucrose: 2.0M
2) mannitol: 1.0M, 1.5M, 2.0M
3) sodium glutamate: 1.5M, 2.0M
4) magnesium sulfate: 1.0M, 1.5M, 2.0M Only sucrose and mannitol at low concentrations (<0.8M) gave good lyophilized cakes. The others either melted back or were not "cake-like." As for those that were reconstituted, all but mannitol had a reconstitution time of less than 20 minutes (FIG. 6). The reconstitution time of sucrose did not vary within the range of concentrations examined, whereas that of sodium glutamate decreased with increasing concentration. However, mannitol had the opposite effect. Overall, this study demonstrates that sucrose is an appropriate excipient to reduce gel reconstitution time to approximately 10 minutes.

5. Study No. 3

Figure 7:
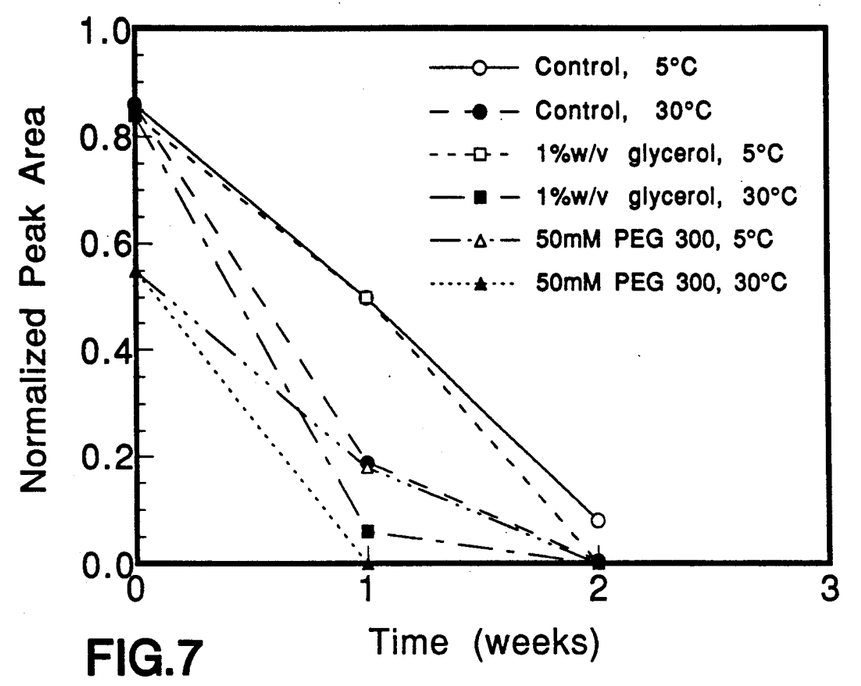
FIG. 7 depicts the stability of relaxin in 3.5% (w/v) hydroxyethyl cellulose gels containing glycerol or PEG 300 at 5° C. or 30° C. as measured by reverse-phase HPLC.
Figure 8:
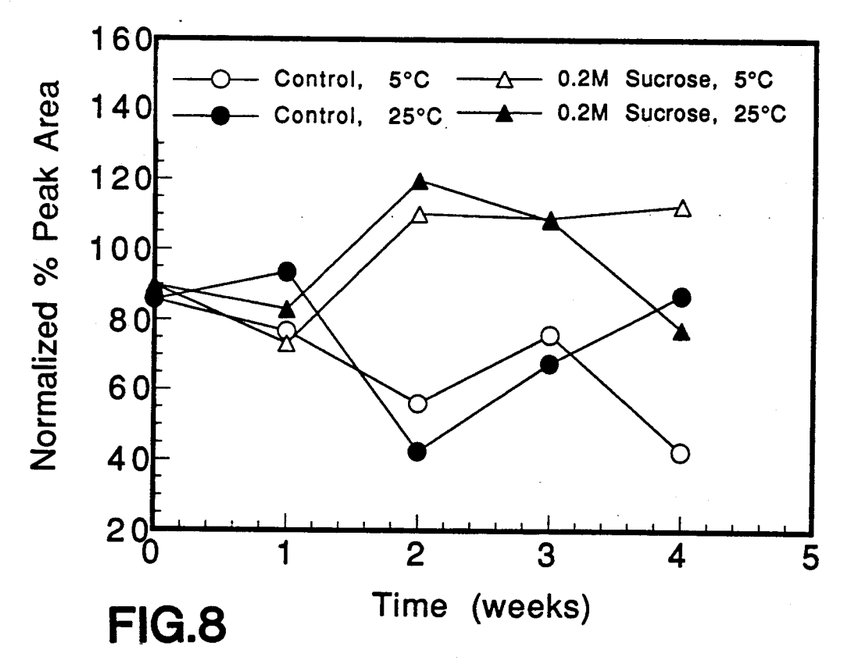
FIG. 8 represents a graph of the stability of relaxin in 3.5% (w/v) hydroxyethyl cellulose gels containing different excipients at 5° or 25° C. as measured by reverse-phase HPLC.
Figure 9:
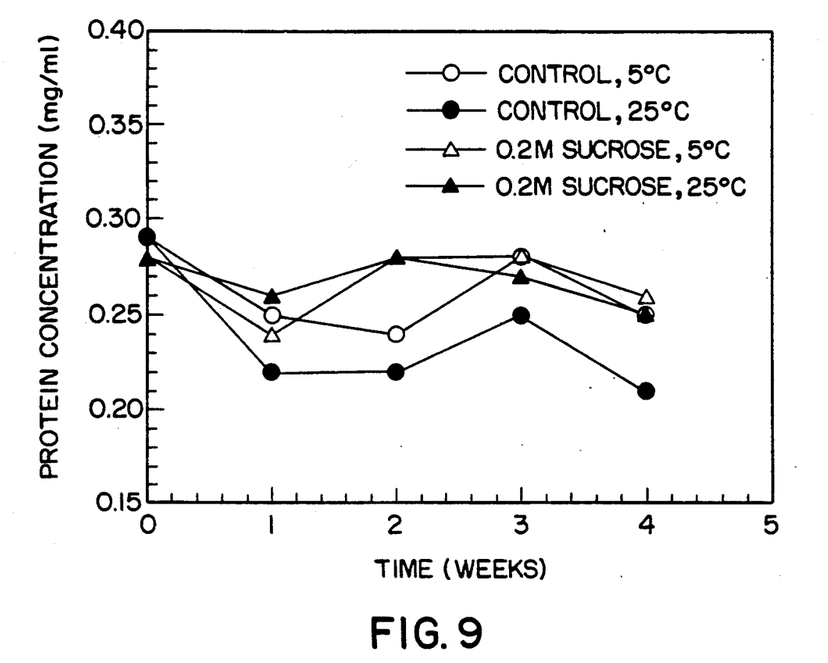
FIG. 9 represents a graph of the stability of relaxin in 3.5% (w/v) hydroxyethyl cellulose gels containing different excipients at 5° or 25° C. as measured by ELISA.

The results from this study indicate that neither PEG nor glycerol protected the relaxin protein from degrading compared to the control at all time points (FIG. 7). However, sucrose shows the ability to protect relaxin (FIG. 8). The ELISA assay confirms this result (FIG. 9).

EXAMPLE 2

This example illustrates the invention utilizing tissue factor as the protein.

A. Size-Exclusion HPLC Assay for Tissue Factor

Instrument: HP 1090

Column: pharmacia Superose 12

Flow Rate: 0.5 ml/min
Mobile Phase: 0.8% (w/v) octylglucoside, 0.01M NaPO$_4$, 0.15M NaCl, pH 7.3
Injection Volume: 50 µl
Protein Concentration: 0.1 mg/ml
UV Detector: 214 nm
Run Time: 45 min
Post Time: 15 min
Temperature: Ambient

B. Tissue Factor Chromogenic Assay

This assay determines the relative enzymatic activity in absorbance units of recombinant tissue factor per milliliter. The liquid tissue factor and the liquid gel were diluted with assay diluent (50 mM Tris.HCl, 100 mM NaCl, 0.1% BSA, and 0.01% thimerosal) and then with relipidation buffer (800 µL thimerosal, 25 µl 1 100 mM CdCl$_2$, and 50 µl of a mixture of 0.5 g phosphatidylcholine and q.s. to 100 ml of deoxycholate) to 4 ng/ml, 2 ng/ml, and 0.5 ng/ml. Duplicate samples were then submitted for analysis. The chromogenic tissue factor assay employed is described in col. 10 of U.S. Pat. No. 5,017,556 issued May 21, 1991.

C. Study No. 4: Effects of PEG and Glycerol on Gel Containing Tissue Factor

Tissue factor was obtained as described in EP 278,776 published 17 Aug. 1988 and formulated in 1.1% octylglucoside in a buffer at pH 7.2. In this study both the protein and the buffer were concentrated about threefold. The protein in hydroxyethyl cellulose gel was initially submitted for the tissue factor chromogenic assay described above to determine the feasibility of such a study. With promising results from this assay a size-exclusion HPLC stability study was set up. The same excipients and amounts thereof as were used in the relaxin Study No. 3 were employed, as well as 50 mM PEG 3350. The two grades of PEG (300 and 3350) exist as a liquid and as a solid, respectively, at room temperature. The protein concentration used in this study was 1 mg/ml. A three-week stability study of the reconstituted gel was set up. The gels were lyophilized with primary drying at $-40°$ C. for 55 hours.

D. Results

Figure 10:
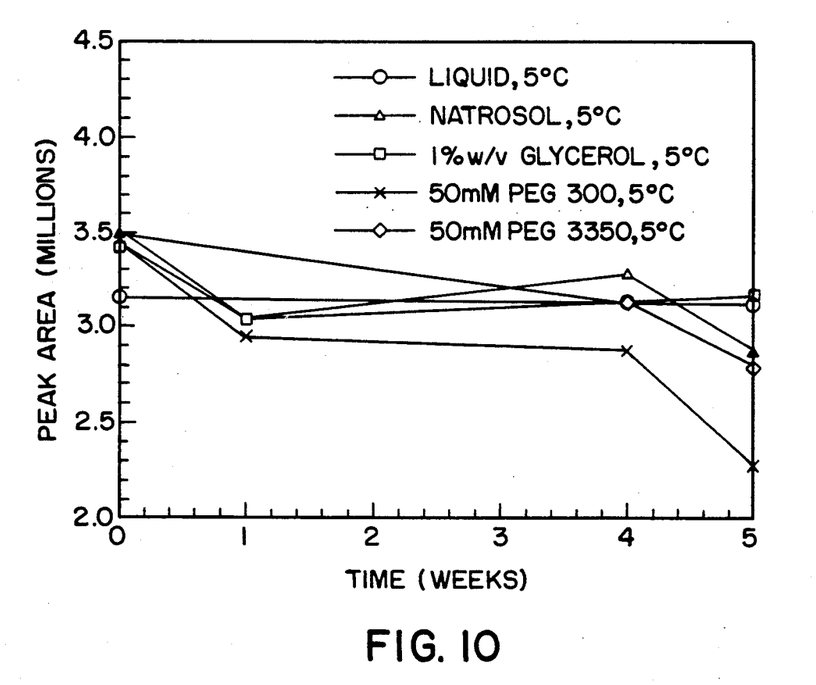
FIG. 10 represents a graph of the stability of tissue factor in 3.5% (w/v) hydroxyethyl cellulose gels containing glycerol or different grades of PEG at 5° C. as measured by size-exclusion HPLC.

This study demonstrates that glycerol protected the tissue factor protein from degradation in a lyophilized gel formulation during a 5° C. storage. The two grades of PEG, on the other hand, did not show any protective properties for this protein. See FIG. 10.

EXAMPLE 3

This example illustrates the invention utilizing TGF-$\beta$ as the protein.

A. Reverse-Phase HPLC Assay for TGF-$\beta$

Instrument: HP 1090
Column: Vydac C4
Mobile Phase: A) 0.1% TFA in water, B) 0.1% TFA in acetonitrile
Gradient: 27% to 35% B in 35 minutes
Flow Rate: 0.5 ml/min
Injection Volume: 200 µl
UV Detector: 214 nm
Run Time: 60 minutes
Post Time: 15 minutes
Temperature: 40° C.

B Study No. 5: Effects of Sucrose on Gel Containing TGF-$\beta$

Liquid TGF-$\beta$ was added to premixed hydroxyethyl cellulose gel as described above to reach a final protein concentration of 0.5 mg/ml, hydroxyethyl cellulose concentration of 3.5% w/v, and sucrose concentration of 0.2M. The gel was then lyophilized and the resulting cakes were stored at 5° C. After a period of storage the lyophilized gel sample was reconstituted with water and assayed with the reverse-phase HPLC assay described above.

C. Results

After eight days of storage at 5° C. the lyophilized gel product still maintained about 90% peak area of the liquid bulk standard, suggesting that sucrose is a likely candidate excipient for stabilizing TGF-$\beta$ in the lyophilized hydroxyethyl cellulose gel.

Conclusions

A. Reconstitution

Of the ten excipients examined, sucrose, sodium glutamate, and magnesium sulfate reconstitute the lyophilized gel in under 10 minutes while the others may take up to 2 hours. For sodium glutamate and PEG, the higher the concentration the shorter the reconstitution time. On the other hand, mannitol had the opposite effect. Also, the higher the molecular weight of PEG, the shorter its reconstitution time. As for glycerol, even though gels at the higher concentration have a reasonable reconstitution time, cake appearance is not acceptable.

B. Protein Stability

The results from the various studies conducted show that lyophilized gel is a stable environment for storing proteins if an appropriate excipient is selected. However, the excipient is protein specific. For example, glycerol keeps tissue factor stable in the lyophilized Natrosol gel, but such results were not observed with relaxin. Sucrose, on the other hand, stabilizes relaxin in a similar environment.

Summary

Based on the results from these reconstitution and protein stability studies, it is apparent that proteins can be formulated with cellulose derivatives and lyophilized so as to obtain gels suitable for topical applications. As to excipients for the proteins, sucrose is a preferred candidate for relaxin and TGF-$\beta$, whereas glycerol is a preferred candidate for tissue factor, based on their ability both to preserve protein stability and allow rapid reconstitution of the lyophilized mixture to form a gel.

What is claimed is:

1. A formulation comprising tissue factor, glycerol, and a water-soluble etherified cellulose in an amount that upon reconstitution of the mixture will form a topical gel.

2. The formulation of claim 1 wherein the glycerol concentration in the reconstituted gel is about 1–4% weight/volume.

3. The formulation of claim 2 wherein the tissue factor concentration in the reconstituted gel is about 0.2 to 1 mg/ml.

4. The formulation of claim 1 wherein the etherified cellulose is hydroxyethylcellulose or methylcellulose.

5. The formulation of claim 1 that is reconstituted to a gel with sufficient water.

6. The formulation of claim 5 wherein the etherified cellulose is present in an amount of about 1–10% by weight/volume of the gel.

7. The formulation of claim 6 wherein the etherified cellulose is hydroxyethylcellulose in an amount of about 1–5% by weight/volume of the gel.

8. The formulation of claim 7 wherein the hydroxyethylcellulose is present in an amount of about 3–4% by weight/volume of the gel.

9. A multi-unit package comprising, in one unit, the formulation of claim 1, and in another unit, a diluent for the formulation.

10. A dual-compartment syringe wherein one compartment contains the formulation of claim 1 and the other compartment contains a diluent for the formulation.

11. A method for treating tissue comprising the steps of:

(a) providing a formulation comprising a lyophilized mixture of tissue, factor, glycerol, and a water-soluble etherified cellulose in an amount that upon reconstitution of the mixture will form a topical gel, (b) reconstituting the mixture in a sufficient amount of water to form a gel, and (c) applying a therapeutically effective amount of the gel topically to the tissue.

12. The method of claim 11 wherein the tissue is skin.

13. A method of modulating the reproductive physiology of mammals during pregnancy and parturition comprising administering to the cervix or vagina a therapeutically effective amount of a gel that has been reconstituted from a formulation comprising a lyophilized mixture of relaxin, sucrose, and a water-soluble etherified cellulose in an amount that upon reconstitution of the mixture will form a topical gel.

* * * * *